United States Patent [19]

Hara et al.

[11] Patent Number: 5,077,442

[45] Date of Patent: Dec. 31, 1991

[54] METHOD FOR PRODUCING 1,4-BUTANEDIOL

[75] Inventors: Yoshinori Hara; Hiroko Inagaki, both of Machida, Japan

[73] Assignee: Mitsubishi Kasei Corporation, Tokyo, Japan

[21] Appl. No.: 683,798

[22] Filed: Apr. 11, 1991

[30] Foreign Application Priority Data

Apr. 26, 1990 [JP] Japan ................... 2-108821

[51] Int. Cl.$^5$ .................. C07C 29/149; C07C 31/20
[52] U.S. Cl. .......................................... 568/864
[58] Field of Search .................................. 568/864

[56] References Cited

U.S. PATENT DOCUMENTS 4,482,764 11/1984 Herrmann et al. ................... 568/864

FOREIGN PATENT DOCUMENTS 2819593 11/1979 Fed. Rep. of Germany ...... 568/864
13527 1/1983 Japan .................................. 568/864

Primary Examiner—J. E. Evans
Attorney, Agent, or Firm—Oblon, Spivak, McClelland, Maier & Neustadt

[57] ABSTRACT

A method for producing 1,4-butanediol by hydrogenating succinic anhydride, succinic acid or γ-butyrolactone in the presence of a catalyst, wherein the hydrogenation reaction is conducted in a liquid phase using as the catalyst a ruthenium type catalyst comprising ruthenium, an organic phosphine and a phosphorus compound of the following formula (1):

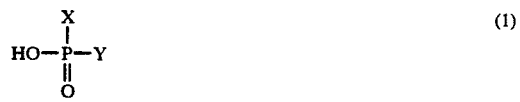

wherein each of X and Y is an atom or a group selected from the group consisting of a hydrogen atom, a hydroxyl group, a halogen atom, an alkoxy group, an alkyl group and an aryl group.

15 Claims, No Drawings

METHOD FOR PRODUCING 1,4-BUTANEDIOL

The present invention relates to a method for producing 1,4-butanediol. More particularly, it relates to an improvement of a method for producing 1,4-butanediol from succinic anhydride, succinic acid or γ-butyrolactone.

1,4-butanediol is useful as a starting material for the production of polybutylene terephthalate or polyurethane. Many proposals have been made for a process for producing 1,4-butanediol by hydrogenating succinic anhydride, succinic acid or γ-butyrolactone. for example, it is known to conduct the hydrogenation reaction in a fixed bed system or in a suspension phase using a solid catalyst such as a copper-chromium type catalyst (Japanese Unexamined Patent Publications No. 20995/1975 and No. 155231/1987), a copper-zinc type catalyst (U.S. Pat. No. 4,048,196 and Japanese Unexamined Patent Publication No. 25434/1991), a copper-molybdenum type catalyst (Japanese Unexamined Patent Publication No. 32191/1979) a nickel type catalyst (U.S. Pat. No. 3,370,067) and a ruthenium oxide type catalyst (Japanese Unexamined Patent Publication No. 109736/1982).

However, conventional methods employing such catalysts, had drawbacks that the reaction conditions were rather severe, and the catalytic activities and the selectivities were not yet adequate. Under the circumstances, the present inventors have previously proposed a method wherein hydrogenation is conducted in a liquid phase using a ruthenium type catalyst containing ruthenium and an organic phosphine (Japanese Unexamined patent Publication No 290640/1990). According to this method, the hydrogenation reaction can be conducted under mild conditions, but the reaction activities have not yet been adequate, and a further improvement has been desired. Further, in this method, an improvement in the activities is observed when ammonium hexafluorophosphate is added as an activity-promoting agent, but there have been problems such as corrosion of the reactor material or modification of the activity-promoting agent due to water present in the reaction system.

It is an object of the present invention to solve such problems of the conventional methods and to provide a method for producing 1,4-butanediol efficiently and in good yield by hydrogenating succinic anhydride, succinic acid or γ-butyrolactone under mild conditions.

The present inventor have conducted extensive studies to accomplish the above object and as a result, have found that in the production of 1,4-butanediol by hydrogenating succinic anhydride, succinic acid or γ-butyrolactone in a liquid phase, the desired product can be obtained under mild conditions in good yield when a ruthenium type catalyst composed of certain specific components is employed. The present invention has been accomplished by this discovery. Thus, the present invention provides a method for producing 1,4-butanediol by hydrogenating succinic anhydride, succinic acid or γ-butyrolactone in the presence of a catalyst, wherein the hydrogenation reaction is conducted in a liquid phase using as the catalyst a ruthenium type catalyst comprising ruthenium, an organic phosphine and a phosphorus compound of the following formula (1):

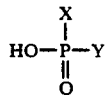

wherein each of X and Y is an atom or a group selected from the group consisting of a hydrogen atom, a hydroxyl group, a halogen atom, an alkoxy group, an alkyl group and an aryl group.

Now, the present invention will be described in detail with reference to the preferred embodiments.

As the starting material of the present invention, succinic anhydride, succinic acid and γ-butyrolactone may be used alone or in combination as a mixture. It is particularly preferred to employ γ-butyrolactone alone, or a mixture of γ-butyrolactone and succinic anhydride. When succinic anhydride is used as the starting material, part of the succinic anhydride is believed to be converted to succinic acid in the reaction system by water produced as a byproduct when the succinic anhydride is hydrogenated to form γ-butyrolactone.

In the present invention, the following catalyst components (a), (b) and (c) are used.

(a) Ruthenium

In the present invention, the ruthenium constituting the ruthenium catalyst may be metal ruthenium or a ruthenium compound. The ruthenium compound may be an oxide, hydroxide, inorganic salt, organic salt or complex compound of ruthenium. Specifically, it includes, for example, ruthenium dioxide, ruthenium tetraoxide, ruthenium dihydroxide, ruthenium chloride, ruthenium bromide, ruthenium iodide, ruthenium nitrate, ruthenium acetate, ruthenium acetylacetonate, sodium hexachlororuthenate, dipotassium tetracarbonyl ruthenate, pentacarbonyl ruthenium, cyclopentadiphenyldicarbonyl ruthenium, dibromotricarbonyl ruthenium, chlorotris(triphenylphosphine)hydridoruthenium, bis(tri-n-butylphosphine)tricarbonyl ruthenium, dodecacarbonyl triruthenium, tetrahydridodecacarbonyl tetraruthenium, dicesium octadecacarbonylhexaruthenate and tetraphenylphosphonium undecacarbonyl hydrotriruthenate. Such metal ruthenium or a ruthenium compound is used usually in an amount of from 0.0001 to 100 mmol, preferably from 0.001 to 10 mmol, as ruthenium, per 1 of the reaction solution.

(b) Organic phosphine

In the present invention, it is necessary to use an organic phosphine as a catalyst component. The organic phosphine is considered to contribute to the control of the electron state of ruthenium as the main catalyst or to the stabilization of the active state of ruthenium. Specific examples of such an organic phosphine include a trialkylphosphine such as tri-n-octylphosphine, tri-n-butylphosphine or dimethyl-n-octylphosphine, a tricycloalkylphosphine such as tricyclohexylphosphine, a triarylphosphine such as triphenylphosphine, an alkylaryl phosphine such as dimethylphenylphosphine and a polyfunctional phosphine such as 1,2-bis(diphenylphosphino)ethane. The organic phosphine is used usually in an amount of from 0.1 to 1,000 mols preferably from 1 to 100 mols, per mol of of ruthenium. The organic phosphine may be supplied to the reaction system by itself or in the form of a composite with the ruthenium catalyst.

(c) Phosphorus compound of the following formula (1)

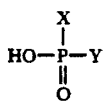

(1)

wherein each of X and Y is an atom or a group selected from the group consisting of a hydrogen atom, a hydroxyl group, a halogen atom, an alkoxy group, an alkyl group and an aryl group.

In the present invention, it is essential to use the phosphorus compound of the above formula (1) as a catalyst component together with the ruthenium component (a) and the organic phosphine component (b). It is thereby possible not only to conduct the hydrogenation reaction under mild conditions while making the best use of the merits of ruthenium as the main component of the catalyst, but also to improve the catalytic activities. In the formula (1), the alkoxy group may, for example, be a methoxy group, an ethoxy group, a propoxy group, a butoxy group, a hexyloxy group or an octyloxy group; the alkyl group may, for example, be a methyl group, an ethyl group, a propyl group, a butyl group, a hexyl group or an octyl group; and the aryl group may, for example, be a phenyl group or a naphthyl group.

Specific examples of such a phosphorus compound include phosphoric acid, phosphorous acid, hyphophosphorous acid, fluorophosphoric acid, dimethyl phosphate, dibutyl phosphate, diphenyl phosphate, dimethyl phosphite, diphenyl phosphite, dimethylphosphinic acid, diphenylphosphinic acid, phenylphosphinic acid, methylphosphonic acid and butylphosphonic acid. Further, phosphorus pentoxide or polyphosphoric acid which is capable of forming phosphoric acid when reacted with water present in the reaction system, may be used instead of phosphoric acid. Further, the phosphorus compound of the formula (1) may be used in the form of a derivative such as an alkali metal salt, an alkaline earth metal salt, an ammonium salt or a phosphonium salt. Such a phosphorus compound of the formula (1) is used usually within a range of from 0.01 to 1,000 mols, preferably from 0.1 to 100 mols, per mol of ruthenium.

The ruthenium type catalyst of the present invention may contain a neutral ligand, as the case requires, in addition to the above components (a), (b) and (c). Such neutral ligand may, for example, be an olefin such as ethylene, propylene, butene, cyclopentene, cyclohexene, butadiene, cyclopentadiene, cyclooctadiene or norbornadiene; an oxygen-containing compound such as carbon monooxide, diethyl ether, anisole, dioxane, tetrahydrofuran, acetone, acetophenone, benzophenone, cyclohexanone, propionic acid, caproic acid, butyric acid, benzoic acid, ethyl acetate, allyl acetate, benzyl benzoate or benzyl stearate; a nitrogen-containing compound such as nitrogen oxide, acetonitrile, propionitrile, benzonitrile, cyclohexylisonitrile, butylamine, aniline, toluidine, triethylamine, pyrrole, pyridine, N-methylformamide, acetoamide, 1,1,3,3-tetramethylurea, N-methylpyrrolidone, caprolactam or nitromethane; a sulfur-containing compound such as carbon disulfide, n-butylmercaptan, thiophenol, dimethyl sulfide, dimethyl disulfide, thiophene, dimethyl sulfoxide or diphenyl sulfoxide; or a phosphorus-containing compound other than an organic phosphine such as tributhylphosphineoxide, ethyldiphenylphosphineoxide, triphenylphosphineoxide, diethylphenylphosphinate, diphenylmethylphosphinate, o,o-dimethylmethylphosphonothiolate, triethylphosphite, triphenylphosphite, triethylphosphate, triphenylphosphate or hexamethylphosphoric triamide.

The method of the present invention is conducted in a uniform liquid phase. Here, a starting material for reaction or a reaction product may be used as a solvent, but other solvent may be employed. Such solvent may, for example, be an ether such as diethyl ether, anisole, tetrahydrofuran, tetraethylene glycol dimethyl ether, ethylene glycol diethyl ether or dioxane; a ketone such as acetone, methyl ethyl ketone or acetophenone; an alcohol such as methanol, ethanol, n-butanol, n-octanol, benzylalcohol, ethylene glycol or diethylene glycol; a carboxylic acid such as formic acid, acetic acid, propionic acid or toluic acid; an ester such as methyl acetate, n-butyl acetate or benzyl benzoate; an aromatic hydrocarbon such as benzene, toluene, xylene, ethylbenzene or tetralin; an aliphatic hydrocarbon such as n-hexane, n-octane, cyclohexane or phenylcyclohexane; a halogenated hydrocarbon such as dichloromethane, trichloroethane or chlorobenzene; a nitrated hydrocarbon such as nitromethane or nitrobenzene; a carboxylic acid amide such as N,N-dimethylformamide, N,N-dimethylacetamide or N-methylpyrrolidone; other amides such as hexamethyl phosphoric acid triamide or N,N,N',N'-tetraethylsufamide; sulfone such as N,N'-dimethylimidazolidone, a urea such as N,N,N,N-tetramethylurea; a sulfone such as dimethylsulfone or tetramethylene sulfone; a sulfoxide such as dimethyl sulfoxide or diphenyl sulfoxide; a polyether such as tetraglyme or 18-crown-6, a nitrile such as acetonitrile or benzonitrile; or a carbonic acid ester such as dimethyl carbonate or ethylene carbonate.

To conduct the hydrogenation reaction in accordance with the method of the present invention, succinic anhydride, succinic acid or γ-butyrolactone, the above mentioned catalyst components and, if necessary, a solvent are charged into a reactor, and hydrogen is introduced thereto. The hydrogen may be diluted with a gas inert to the reaction, such as nitrogen or carbon dioxide. The reaction temperature is usually from 50° to 250° C., preferably from 100° to 200° C. When the reaction is conducted on an industrial scale, the hydrogen pressure in the reaction system is usually from 0.1 to 200 kg/cm$^2$, preferably from 1 to 150 kg/cm$^2$. The reaction may be conducted in a batch system or in a continuous system. In the case of a batch system, the required reaction time is usually from 1 to 20 hours. When succinic anhydride or succinic acid is used as the starting material, water will be formed as a byproduct, as the reaction proceeds. If the reaction is conducted while removing such byproduct water out of the reaction system by a reaction mode such as stripping, for example, by continuously circulating hydrogen in the reaction system, a further improved reaction activity can be attained. After completion of the reaction, desired 1,4-butanediol can be obtained from the reaction solution by a usual separating means such as distillation or extraction. The distillation residue can be recycled as a catalyst component to the reaction system.

Now, the present invention will be described in further detail with reference to Examples. However, it should be understood that the present invention is by no means restricted to such specific Examples.

In the following Examples, the selectivity and yield of the product (1,4-butanediol or tetrahydrofuran) in a case where γ-butyrolactone was used as the starting material for the reaction, were defined as follows.

Selectivity for the product (%)=A/B×100 where A is the amount (mmol) of the product, and B is the conversion (mmol) of γ-butyrolactone.

Yield of the product (%)=A/C×100 where A is the amount (mmol) of the product, and C is the charged amount (mmol) of γ-butyrolactone.

On the other hand, in a case where both succinic anhydride and γ-butyrolactone were used as the starting materials for reaction, the selectivity for the product (1,4-butanediol or tetrahydrofuran) and the selectivity for γ-butyrolactone were defined as follows.

Selectivity for the product (%)=D/E×100 where D is the amount (mmol) of the product, and E is a total amount of the conversion (mmol) of succinic anhydride and the charged amount (mmol) of γ-butyrolactone.

Selectivity for γ-butyrolactone (%)=F/G×100 where F is the remaining amount (mmol) of γ-butyrolactone, and G is the total amount of the conversion (mmol) of succinic anhydride and the charged amount (mmol) of γ-butyrolactone.

EXAMPLE 1

Into a 200 ml SUS autoclave equipped with an induction stirrer, 0.25 mmol of ruthenium acetylacetonate, 2.5 mmol of trioctylphosphine, 0.625 mmol of phospholic acid, 392.5 mmol of γ-butyrolactone and 70 ml of tetraethylene glycol dimethyl ether (solvent) were charged, and the autoclave was flashed with nitrogen gas and heated to a temperature of 200° C.

Then, 50 kg/cm$^2$ of hydrogen gas was injected, and a hydrogenation reaction was conducted for 3 hours. After completion of the reaction, the reaction product was analyzed by gas chromatography, whereby the conversion of γ-butyrolactone was 45.8%, and the amount of 1,4-butanediol formed was 135.6 mmol. The yield of 1,4-butanediol was 34.6%, and the selectivity was 75.5%. Further, 2.3 mmol of tetrahydrofuran and 3.7 mmol of n-butanol were found as byproducts.

EXAMPLE 2

The operation was conducted in the same manner as in Example 1 except that 0.625 mmol of hypophosphorous acid was used instead of phosphoric acid used in Example 1, whereby the conversion of γ-butyrolactone was 36.6% and the amount of 1,4-butanediol formed was 123.6 mmol. The yield of 1,4-butanediol was 31.5%, and the selectivity was 86.1%. Further, the amounts of tetrahydrofuran and n-butanol formed as byproducts were 1.1 mmol and 3.0 mmol, respectively.

EXAMPLE 3

The hydrogenation reaction was conducted in the same manner as in Example 1 except that 70 ml of m-xylene was used instead of tetraethylene glycol dimethyl ether solvent used in Example 1. After completion of the reaction, the autoclave was opened, and two separated layers were observed. The upper layer was composed mainly of m-xylene, and the lower layer was composed mainly of the product 1,4-butanediol. The reaction product was analyzed, whereby the conversion of γ-butyrolactone was 50.4%, and the amount of 1,4-butanediol formed was 158.2 mmol. The yield of 1,4-butanediol was 40.3%, and the selectivity was 80.0%. Further, the amounts of tetrahydrofuran and n-butanol formed as byproducts were 2.5 mmol and 0.9 mmol, respectively.

EXAMPLE 4

The operation was conducted in the same manner as in Example 1 except that 0.625 mmol of phosphorous acid instead of phosphoric acid used in Example 1, whereby the conversion of γ-butyrolactone was 42.4%, and the amount of 1,4-butanediol formed was 125.7 mmol. The yeild of 1,4-butanediol was 32.0%, and the selectivity was 75.5%. Further, the amounts of tetrahydrofuran and n-butanol formed as byproducts were 1.0 mmol and 0.8 mmol, respectively.

EXAMPLE 5

The operation was conducted in the same manner as in Example 1 except that 0.625 mmol of phenyl phosphonic acid was used instead of phosphoric acid used in Example 1, whereby the conversion of γ-butyrolactone was 53.3%, and the amount of 1,4-butanediol formed was 159.9 mmol. The yeild of 1,4-butanediol was 40.7%, and the selectivity was 76.4%. Further, the amounts of tetrahydrofuran and n-butanol formed as byproducts were 2.0 mmol and 0.6 mmol, respectively.

COMPARATIVE EXAMPLE 1

The operation was conducted in the same manner as in Example 1 except that phosphoric acid used in Example 1 was not employed, whereby the conversion of γ-butyrolactone was 25.5%, and the amount or 1,4-butanediol formed was 80.5 mmol. The yield of 1,4-butanediol was 20.5%, and the selectivity was 80.4%. Further, the amounts of tetrahydrofuran and n-butanol formed as byproducts were 1.0 mmol and 3.3 mmol, respectively.

COMPARATIVE EXAMPLE 2

The operation was conducted in the same manner as in Example 1 except that 0.625 mmol of ammonium hexafluorophosphate was used instead of phosphoric acid used in Example 1, whereby the conversion of γ-butyrolactone was 30.7%, and the amount of 1,4-butanediol formed was 96.9 mmol. The yeild of 1,4-butanediol was 24.7%, and the selectivity was 80.5%. Further, the amounts of tetrahydrofuran and n-butanol formed as byproducts were 3.0 mmol and 1.9 mmol, respectively.

EXAMPLE 6

Into a 70 ml microautoclave equipped with spinner stirrer, 0.1 mmol of ruthenium acetylacetonate, 1.0 mmol trioctyl phosphine 1 mmol of phenylphosphonic acid (a phosphorus compound of the above formula (1) wherein X is a phenyl group and Y is a hydroxyl group), 30.0 mmol of γ-butyrolactone, 30.0 mmol of succinic anhydride and 14 ml of m-xylene (solvent) were charged, and the autoclave was flashed with nitrogen gas. Then, 70 kg/cm$^2$ of hydrogen was injected at room temperature. The autoclave was heated, and a hydrogenation reaction was conducted at 210° C. for 6 hours. After completion of the reaction, the reaction product was analyzed by gas chromatography, whereby the composition of the product was found to be 29.0 mmol of γ-butyrolactone, 0.9 mmol of tetrahydrofuran as byproduct and 24.0 mmol of 1,4-butanediol.

EXAMPLE 7

The reaction was conducted in the same manner as in Example 6 except that 1 mmol of n-butylphosphonic acid (a phosphorus compound of the above formula (1) wherein X is a butyl group and Y is a hydroxyl group) was used instead of the phosphorus compound used in Example 6. After completion of the reaction, the product was analyzed, whereby the composition of the product was found to be 36.4 mmol of γ-butyrolactone, 1.4 mmol of tetrahydrofuran as byproduct and 18.7 mmol of 1,4-butanediol.

EXAMPLE 8

The reaction was conducted in the same manner as in Example 6 except that 1 mmol of dibutyl phosphate (a phosphorus compound of the above formula (1) wherein each of X and Y is a butoxy group) was used instead of the phosphorus compound used in Example 6. After completion of the reaction, the reaction product was analyzed by gas chromatography, whereby the composition of the product was found to be 25.5 mmol of γ-butyrolactone, 4.0 mmol of tetrahydrofuran as byproduct, and 27.3 mmol of 1,4-butanediol.

EXAMPLE 9

Into a 200 ml SUS autoclave equipped with an induction stirrer, 0.5 mmol of ruthenium acetylacetonate, 5.0 mmol of trioctylphosphine, 5 mmol of phenylphosphonic acid, 150 mmol of succinic anhydride, 150 mmol of γ-butyrolactone and as solvents, 20 ml of toluene and 50 ml of phenylcyclohexane, were charged, and the autoclave was flashed with nitrogen gas and heated to a temperature of 210° C. Then, 50 kg/cm$^2$ of hydrogen gas was injected, and a hydrogenation reaction was conducted for 3 hours at a flow rate of GHSV 250 h$^{-1}$. After completion of the reaction, the reaction product was analyzed by titration, whereby the conversion of succinic anhydride was 99.4%. Further, the product was analyzed by gas chromatography, whereby the selectivity for 1,4-butanediol was 31.8%, the selectivity for tetrahydrofuran was 2.7%, and the selectivity for γ-butyrolactone was 64.1%.

EXAMPLE 10

The reaction was conducted in the same manner as in Example 1 except that the reaction pressure 50 kg/cm$^2$ adopted in Example 9 was changed to 120 kg/cm$^2$, whereby the conversion of succinic anhydride was 97.4%. Further, the selectivity for 1,4-butanediol was 67.2%, the selectivity for tetrahydrofuran was 3.2%, and the selectivity for γ-butyrolactone was 29.1%.

EXAMPLE 11

The reaction was conducted in the same manner as in Example 9 except that 5 mmol of dibutyl phosphate was used instead of phenylphosphonic acid used in Example 9, whereby the conversion of succinic anhydride was 99.6%, the selectivity for 1,4-butanediol was 41.9%, selectivity for tetrahydrofuran was 1.7%, and the selectivity for γ-butyrolactone was 50.8%.

EXAMPLE 12

The reaction was conducted in the same manner as in Example 9 except that 5 mmol of dibutylphosphate was used instead of phenylphosphonic acid used in Example 9, and the reaction pressure was changed to 80 kg/cm$^2$, whereby the conversion of succinic anhydride was 99.8%, the selectivity for 1,4-butanediol was 51.6%, the selectivity for tetrahydrofuran was 2.4% and the selectivity for γ-butyrolactone was 34.2%.

COMPARATIVE EXAMPLE 3

The reaction was conducted in the same manner as in Example 9 except that 2.5 mmol of ammonium hexafluorophosphate was used instead of phenylphosphonic acid used in Example 9, whereby the conversion of succinic anhydride was 98.9%, the selectivity for 1,4-butanediol was 23.9%, the selectivity for tetrahydrofuran was 0.8%, and selectivity for γ-butyrolactone was 60.9%.

According to the method of the present invention, for the production of 1,4-butanediol by hydrogenation of succinic anhydride, succinic acid or γ-butyrolactone, the reaction is conducted in a uniform liquid phase using a ruthenium type catalyst comprising the above components (a), (b) and (c), whereby the desired product can be produced in good yeild under mild conditions as compared with conventional methods. Therefore, the practical value of the method is significant.

We claim:

1. A method for producing 1,4-butanediol by hydrogenating succinic anhydride, succinic acid or γ-butyrolactone in the presence of a catalyst, wherein the hydrogenation reaction is conducted in a liquid phase using as the catalyst a ruthenium type catalyst comprising ruthenium, an organic phosphine and a phosphorus compound of the following formula (1):

wherein each of X and Y is an atom or a group selected from the group consisting of a hydrogen atom, a hydroxyl group, a halogen atom, an alkoxy group, an alkyl group and an aryl group.

2. The method according to claim 1, wherein a mixture of succinic anhydride and γ-butyrolactone is hydrogenated.

3. The method according to claim 1, wherein the compound of the formula (1) is phosphoric acid, phosphorous acid or hypophosphorous acid.

4. The method according to claim 1, wherein the compound of the formula (1) is a phosphoric acid monoester or a phosphoric acid diester.

5. The method according to claim 1, wherein the compound of the formula (1) is a phosphorous acid diester.

6. The method according to claim 1, wherein the compound of the formula (1) is a phosphinic acid.

7. The method according to claim 1, wherein the compound of the formula (1) is a phosphonic acid.

8. The method according to claim 1, wherein ruthenium is metallic ruthenium or a ruthenium compound.

9. The method according to claim 8, wherein the ruthenium compound is an oxide, hydroxide, inorganic salt, organic salt or complex compound of ruthenium.

10. The method according to claim 1, wherein the ruthenium is present in an amount of from 0.001 to 100 mmol per l of the reaction solution.

11. The method according to claim 1, wherein the molar ratio of (1) ruthenium: (2) the organic phosphine: (3) the phosphorus compound of the formula (1) is 1:0.1–1,000:0.01–1,000.

12. The method according to claim 1, wherein the molar ratio of (1) ruthenium: (2) the organic phosphine: (3) the phosphorous compound of the formula (1) is 1:1–100:0.1–100.

13. The method according to claim 1, wherein the hydrogenation reaction is conducted by continuously supplying hydrogen gas.

14. The method according to claim 1, wherein the reaction temperature is within a range of from 50° to 250° C.

15. The method according to claim 1, wherein the hydrogen pressure in the reaction system is within a range of from 0.1 to 200 kg/cm$^2$.

* * * * *